United States Patent
Gallenkamp et al.

(10) Patent No.: US 6,476,224 B2
(45) Date of Patent: Nov. 5, 2002

(54) METHOD FOR PRODUCING AR(ALK) YLURACILES, NOVEL CORRESPONDING INTERMEDIATE PRODUCTS AND METHOD FOR PRODUCING SAID INTERMEDIATE PRODUCTS

(75) Inventors: Bernd Gallenkamp, Wuppertal (DE); Reinhard Lantzsch, Wuppertal (DE); Lothar Rohe, Wuppertal (DE); Lubbertus Mulder, Hagen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/783,838

(22) Filed: Feb. 14, 2001

(65) Prior Publication Data
US 2002/0022727 A1 Feb. 21, 2002

Related U.S. Application Data

(62) Division of application No. 09/530,992, filed on May 8, 2000, now Pat. No. 6,225,470.

(30) Foreign Application Priority Data
Nov. 13, 1997 (DE) .......................... 197 50 195

(51) Int. Cl.[7] .................. C07D 239/54; C07D 239/46; C07C 275/16; C07C 275/24
(52) U.S. Cl. ................ 544/309; 544/311; 544/312; 544/313; 544/314; 544/63; 544/65; 564/123; 564/155
(58) Field of Search ............... 544/63, 65, 309, 544/311, 312, 313, 314; 564/123, 155

(56) References Cited
U.S. PATENT DOCUMENTS 3,690,863 A * 9/1972 Gerike ................... 71/111
5,593,945 A 1/1997 Andree et al. ........... 504/243
5,681,794 A 10/1997 Andree et al. ........... 504/243

OTHER PUBLICATIONS

Bull. Soc. Chim. Belg. vol. 101, (month unavailable) 1992, pp. 313–321.

Marie–Aimée Decock–Plancquaert et al, Syntheses of New 4–Trifluoromethylated 1,3–Oxazin–6–Ones From the Enamine of Ethyl Trifluoroacetoacetate.

* cited by examiner

Primary Examiner—Richard L. Raymond
Assistant Examiner—Venkataraman Balasubrasubramanian
(74) Attorney, Agent, or Firm—Joseph C. Gil; John E. Mrozinski, Jr.

(57) ABSTRACT

The invention relates to a process for preparing ar(alk)yluracils of the general formula (I)

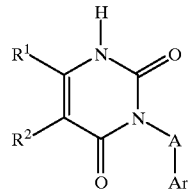

(I)

in which

A represents a single bond or represents alkanedlyl,

Ar represents optionally substituted aryl, $R^1$ represents optionally substituted alkyl and $R^2$ represents hydrogen, halogen or alkyl, and to novel intermediates for this purpose and to processes for their preparation.

5 Claims, No Drawings

METHOD FOR PRODUCING AR(ALK) YLURACILES, NOVEL CORRESPONDING INTERMEDIATE PRODUCTS AND METHOD FOR PRODUCING SAID INTERMEDIATE PRODUCTS

This is a divisional application of Ser. No. 09/530,992, filed May 8, 2000 which now U.S. Pat. No: 6,225,470.

Method for producing ar(alk)yluraciles, novel corresponding intermediate products and method for producing said intermediate products.

The invention relates to a novel process for preparing ar(alk)yluracils, which are known as herbicidally active compounds, to novel intermediates for this purpose and to processes for their preparation.

It is known that certain substituted cyanophenyluracils can be prepared by reacting appropriate aminoalkenoic esters with appropriate cyanophenyl isocyanates or cyanophenylurethanes in the presence of reaction auxiliaries, such as, for example, sodium hydride (cf. EP-A-648749). However, in this procedure, the yield and the quality of the resulting products are not always entirely satisfactory and the reaction components which are required are not particularly suitable for industrial purposes.

Furthermore, it is known that certain substituted phenyluracils can be prepared by reacting appropriate substituted N-phenylaminoalkenamides with suitable carbonic acid derivatives (cf. WO-A-95/32952). However, the synthesis route described in this publication involves many steps and is complicated.

Furthermore, it is known that substituted cyanophenyluracils are obtained by reacting appropriate cyanophenylpyrimidinones with bases and reacting the substituted N-cyanophenyl-aminoalkenamides formed with carbonic acid derivatives, such as, for example, phosgene or diphenyl carbonate (cf. DE-A-19604582). However, the desired products are not always obtained in high yields and in satisfactory quality.

The invention provides (a) a process for preparing ar(alk)yluracils of the general formula (I)

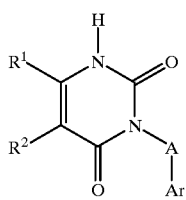

(I)

in which
  A represents a single bond or represents alkanediyl,
  Ar represents optionally substituted aryl,
  $R^1$ represents optionally substituted alkyl and
  $R^2$ represents hydrogen, halogen or alkyl,
characterized in that substituted aminoalkenamides of the general formulae (IIa) or (IIb)

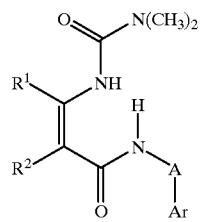

(IIa)

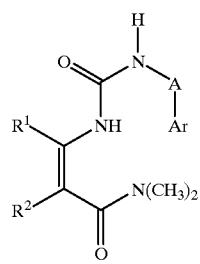

(IIb)

in which

A, Ar, $R^1$ and $R^2$ are as defined above are heated at temperatures between 40° C. and 120° C., if appropriate in the presence of a diluent, (b) novel substituted aminoalkenamides of the general formulae (IIa) or (IIb)

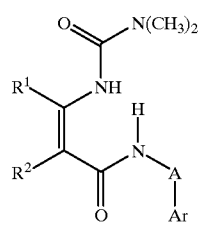

(IIa)

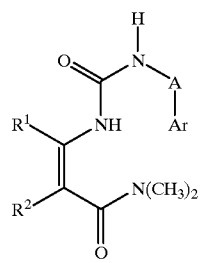

(IIb)

in which

A represents a single bond or represents alkanediyl,
  Ar represents optionally substituted aryl,
  $R^1$ represents optionally substituted alkyl and
  $R^2$ represents hydrogen, halogen or alkyl, (c) a process for preparing substituted aminoalkenamides of the general formula (IIa), characterized in that substituted pyrimidones of the general formula (III)

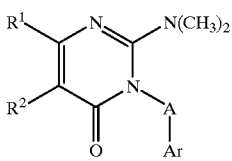

(III)

in which

A, Ar, $R^1$ and $R^2$ are as defined above are reacted at temperatures between 0° C. and 100° C. with an acid, if appropriate in the presence of a diluent, (d) a process for preparing substituted aminoalkenamides of the general formula (IIb), characterized in that substituted oxazinones of the general formula (IV)

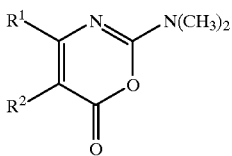

(IV)

in which $R^1$ and $R^2$ are as defined above are reacted with ar(alk)ylamines of the general formula (V)

 (V)

H$_2$N—A—Ar in which

A and Ar are as defined above at temperatures between 0° C. and 150° C., if appropriate in the presence of a diluent, (c) novel substituted pyrimidones of the general formula (III)

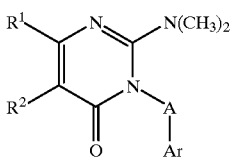

(III)

in which

A represents a single bond or represents alkanediyl,

Ar represents optionally substituted aryl, $R^1$ represents optionally substituted alkyl and $R^2$ represents hydrogen, halogen or alkyl, (f) a process for preparing substituted pyrimidones of the general formula (III), characterized in that substituted aminoalkenamides of the general formula (VI)

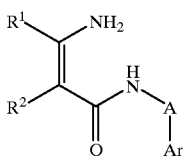

(VI)

in which

A, Ar, $R^1$ and $R^2$ are as defined above are reacted with dichloromethylene-dimethylimmonium chloride of the formula (VII)

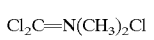 (VII)

Cl$_2$C=N(CH$_3$)$_2$Cl at temperatures between 0° C. and 100° C. in the presence of a diluent.

The invention also provides the novel route for preparing ar(alk)yluracils of the general formula (I) which involves the steps set forth in a general manner above under (f), (c) and (a).

It is surprising that the ar(alk)yluracils of the general formula (I) can be prepared in a simple manner in high yields and good quality by this novel route.

The oxazinones of the general formula (IV), which are to be used, if appropriate, as intermediates are known and/or can be prepared by processes known per se (cf. Bull. Soc. Chim. Belg. 101 (1992), 313–321; Preparation Examples).

The substituted aminoalkenamides of the general formula (VI) to be used, if appropriate, as intermediates are known and/or can be prepared by processes known per se (cf. DE-A-19604582; Preparation Examples).

Preferred meanings in the formulae (I), (IIa), (IIb), (III) and (VI) are

A represents a single bond or represents straight-chain or branched alkanediyl having 1 to 4 carbon atoms, Ar represents phenyl or naphthyl, each of which is optionally substituted by amino, cyano, halogen or the grouping —N(R$^3$)SO$_2$R$^4$, $R^1$ represents optionally fluorine- and or chlorine-substituted alkyl having 1 to 4 carbon atoms, $R^2$ represents hydrogen, fluorine, chlorine, bromine or alkyl having 1 to 4 carbon atoms, $R^3$ represents hydrogen or represents in each case optionally fluorine- and/or chlorine-substituted alkyl, alkylcarbonyl or alkylsulphonyl having in each case 1 to 6 carbon atoms in the alkyl groups, represents in each case optionally fluorine- and/or chlorine-substituted cycloalkylcarbonyl or cycloalkylsulphonyl having in each case 3 to 6 carbon atoms in the cycloalkyl groups, or represents in each case optionally fluorine- and/or chlorine-substituted phenylcarbonyl or phenylsulphonyl, and $R^4$ represents optionally fluorine- and/or chlorine-substituted alkyl having 1 to 6 carbon atoms, represents optionally fluorine- and/or chlorine-substituted cycloalkyl having 3 to 6 carbon atoms, or represents in each case optionally fluorine- and/or chlorine-substituted phenyl.

Particularly preferred meanings in the formulae (I), (IIa), (IIb), (III) and (IV) are A represents a single bond or represents a methylene group, Ar represents phenyl which is optionally substituted by amino, cyano, fluorine, chlorine, bromine or the grouping —N(R$^3$)SO$_2$R$^4$, $R^1$ represents in each case optionally fluorine- and or chlorine-substituted methyl or ethyl, $R^2$ represents hydrogen, fluorine, chlorine, bromine, methyl or ethyl, $R^3$ represents hydrogen or represents in each case optionally fluorine- and/or chlorine-substituted methyl, ethyl, n- or i-propyl, acetyl, propionyl, methylsulphonyl or ethylsulphonyl, represents in each case optionally fluorine- and/or chlorine-substituted cyclopropylcarbonyl, cyclobutylcarbonyl, cyclopentylcarbonyl, cyclohexylcarbonyl, cyclopropylsulphonyl, cyclobutylsulphonyl, cyclopentylsulphonyl or cyclohexylsulphonyl, or represents in each case optionally fluorine- and/or chlorine-substituted phenylcarbonyl or phenylsulphonyl, and $R^4$ represents in each case optionally fluorine- and/or chlorine-substituted methyl, ethyl, n- or i-propyl, n-, i-, s- or t-butyl, represents in each case optionally fluorine- and/or chlorine-substituted cyclopropyl, cyclobutyl, cyclopentyl or cyclohexyl, or represents in each case optionally fluorine- and/or chlorine-substituted phenyl.

The abovementioned general or preferred radical definitions apply both to the end products of the formula (I) and, correspondingly, to the starting materials or intermediates required in each case for the preparation. These radical definitions can be combined with one another at will, i.e. including combinations between the given preferred ranges.

The processes according to the invention described above under (a), (c), (d) and (f) are abbreviated below as "process (a)", "process (c)", "process (d)" and "process (e)".

Using, for example, N-(4-cyano-2,5-difluoro-phenyl)-3-amino-4,4,4-trifluoro-2-butenamide and dichloromethylene-dimethylimmonium chloride as starting materials, reacting the product obtained in their reaction according to process (f), for example, with hydrogen bromide according to process (c) and heating the resulting product according to process (a), the course of the reaction can be illustrated by the following formula scheme:

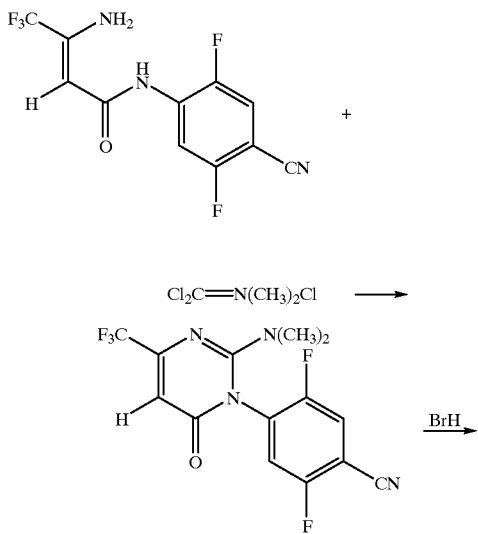

-continued

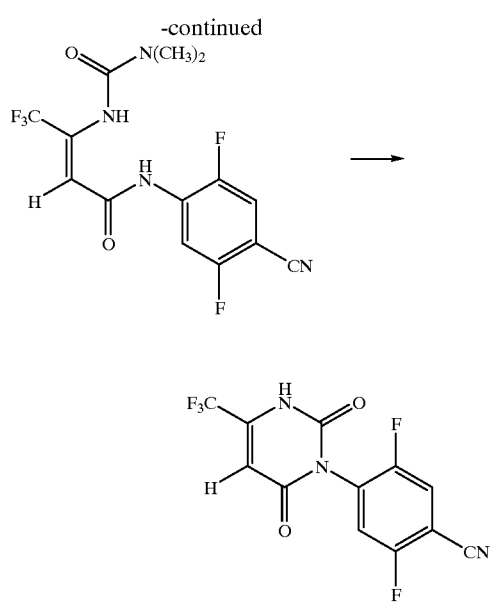

The process (f) according to the invention for preparing compounds of the general formula (III) is carried out using a diluent. Suitable diluents for this purpose are, especially, inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexene, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; carboxylic acids, such as acetic acid or propionic acid, nitriles, such as acetonitrile, propionitrile or butyronitrile; esters, such as methyl acetate or ethyl acetate amides, such as N,N-dimethylformamide, N,N-dimethylacetamide, N-methyl-formanilide, N-methyl-pyrrolidone or hexamethylphosphoric triamide; sulphoxides, such as dimethyl sulphoxide.

When carrying out the process (f) according to the invention, the reaction temperatures can be varied within a relatively wide range. In general, the process is carried out at temperatures between 0° C. and 100° C., preferably between 20° C. and 80° C.

The process (f) according to the invention is generally carried out under atmospheric pressure. However, it is also possible to carry out the process according to the invention under elevated or reduced pressure—generally between 0.1 bar and 10 bar.

For carrying out the process (f) according to the invention, in general from 1.0 to 3.0 mol, preferably from 1.1 to 2.0 mol, of dichloromethylene-dimethylimmonium chloride of the formula (VII) are employed per mole of starting material of the formula (VI).

In a preferred embodiment of the process (f) according to the invention, the dichloromethylene-dimethylimmonium chloride of the formula (VII) is initially charged in a diluent, and a substituted N-cyanophenyl-aminoalkenamide of the general formula (VI) is added a little at a time with stirring at room temperature (about 20° C. to 30° C.). The reaction mixture is then stirred at slightly elevated temperature for several hours until evolution of gas has ceased. Work-up can be carried out by customary methods. The mixture is, for example, stirred with aqueous sodium bicarbonate solution and the organic phase is separated off, washed with aqueous sodium bicarbonate solution and then with water and concentrated under reduced pressure. The product that remains in the residue can be crystallized by digestion with an organic solvent (cf. the Preparation Examples).

The process (c) according to the invention for preparing compounds of the general formula (IIa) is carried out using an acid. In this context, preferred acids are protic acids. These include, for example, hydrogen fluoride, hydrogen chloride, hydrogen bromide, hydrogen iodide, sulphuric acid, phosphoric acid, methanesulplhonic acid, trifluoromethanesulphonic acid, benzenesulphonic acid, p-toluenesulphonic acid, formic acid, acetic acid, propionic acid and trifluoroacetic acid. Very particular preference is given to using hydrogen chloride as acid in the process (c) according to the invention.

The processes (c) and (d) according to the invention are preferably carried out using diluents. Suitable diluents here are, in addition to water, especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; carboxylic acids, such as formic acid, acetic acid or propionic acid, nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters such as methyl acetate or ethyl acetate, sulphoxides, such as dimethyl sulphoxide.

N,N-Dimethylformamide may be mentioned as a particularly preferred diluent for process (c), ethylene glycol dimethyl ether (1,2-dimethoxy-ethane) may be mentioned as a particularly preferred diluent for the processes (d).

When carrying out the processes (c) and (d) according to the invention, the reaction temperatures can in each case be varied within a relatively wide range. In general, the processes are carried out at temperatures between 0° C. and 150° C., preferably between 10° C. and 110° C.

The processes (c) and (d) according to the invention are generally carried out under atmospheric pressure. However, it is also possible to carry out the processes (c) and (d) according to the invention under elevated or reduced pressure—generally between 0.1 bar and 10 bar.

For carrying out the process (c) according to the invention, in general from 0.8 to 1.5 mol, preferably from 0.9 to 1.2 mol. of an acid are employed per mole of cyanophenylpyrimidone of the formula (III).

In a preferred embodiment of the process (c) according to the invention, a cyanophenylpyrimidone of the formula (III) is initially charged in a solvent and, at room temperature (about 20° C. to 30° C.), an acid is slowly metered in. The reaction temperature is then stirred for another few hours and subsequently worked up in a customary manner. The mixture is, for example, poured into ice-water and stirred thoroughly. The product, which is then generally obtained as crystals, can be isolated by filtration with suction (cf. the Preparation Examples).

For carrying out the process (d) according to the invention, in general from 0.8 to 1.5 mol, preferably from 0.9 to 1.2 mol, of an ar(alk)ylamine of the formula (V) are employed per mole of oxazinone of the formula (IV).

In a preferred embodiment of the process (d) according to the invention, an oxazinone of the formula (IV) is mixed with an ar(alk)ylamine of the formula (V) at room temperature in a solvent, and the reaction mixture is stirred at elevated temperature until the reaction has ended. The reaction product is, on cooling, generally obtained as crystals and can be isolated by filtration with suction (cf. the Preparation Examples).

The process (a) according to the invention for preparing compounds of the general formula (I) is preferably carried out using a diluent. Suitable diluents are, especially, inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanonic or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters such as methyl acetate or ethyl acetate, sulphoxides, such as dimethyl sulphoxide.

When carrying out the process (a) according to the invention, the reaction temperatures can be varied within a relatively wide range. In general, the process is carried out at temperatures between 40° C. and 120° C., preferably between 50° C. and 100° C.

The process (a) according to the invention is generally carried out under atmospheric pressure. However, it is also possible to carry out the process according to the invention under elevated or reduced pressure—in general between 0.1 bar and 10 bar.

In a preferred embodiment of the process (a) according to the invention, a substituted aminoalkenamide of the general formulae (IIa) or (IIb) is, at room temperature (about 20° C. to 30° C.), stirred with a diluent, and the mixture is heated with stirring until the reaction has ended. Work-up is then carried out in a customary manner (cf. the Preparation Examples).

The substituted ar(alk)yluracils of the general formula (I) to be prepared according to the invention are already known as herbicidally active compounds (cf. EP-A-648 749).

PREPARATION EXAMPLES

Example (I-1)

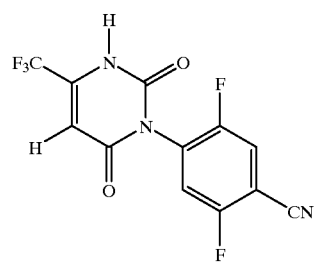

(Process (a))

With stirring, a mixture of 71.0 g (0.17 mol) of N-(4-cyano-2,5-difluoro-phenyl)-3-(dimethylaminocarbonylamino)-4,4,4-trifluoro-2-butenamide and 350 ml of 1,2-dimethoxyethane (ethylene glycol dimethyl ether) is slowly heated to 70° C. and stirred at this temperature for three hours. The mixture is subsequently concentrated under water pump vacuum and, after the residue had been stirred with 85 g of methylene chloride, reconcentrated. The residue is stirred with 765 ml of water and allowed to stand for 30 minutes. Most of the water is then decanted off and the crude product that remains is vigorously ("Ultra-Turrax") stirred with 380 ml of water and filtered. The combined aqueous solutions are admixed dropwise with stirring with 15 ml of conc. hydrochloric acid and the resulting crystalline product is isolated by filtration with suction and dried at 50° C. under reduced pressure.

This gives 49.8 g (92.4% pure, i.e. 87% of theory) of 1-(4-cyano-2,5-difluoro-phenyl)-3,6-dihydro-2,6-dioxo-4-trifluoromethyl-1(2H)-pyrimidine of melting point 208° C.

Example (I-2)

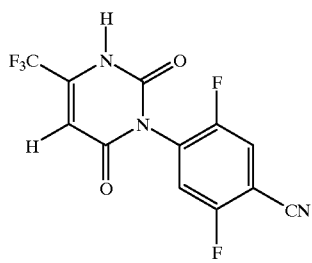

(Process (a))

A mixture of 1.8 g (5 mMol) of N,N-dimethyl-3-(4-cyano-2,5-difluoro-phenyl-amino-carbonylamino)-4,4,4-trifluoro-2-butenamide and 20 ml of acetic acid is heated under reflux for 16 hours and, after cooling, slowly diluted with water to about three times its volume. The resulting crystalline product is isolated by filtration with suction.

This gives 1.25 g (79% of theory) of 1-(4-cyano-2,5-difluoro-phenyl)-3,6-dihydro-2,6-dioxo-4-trifluoromethyl-1(2H)-pyrimidine of melting point 217° C.

Example (IIa-1)

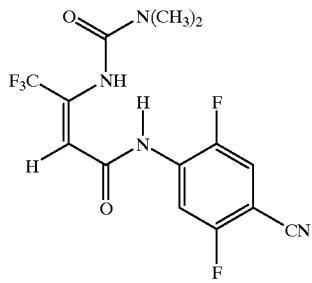

(Process (c))

At room temperature (about 20° C. to 30° C.), a mixture of 73.3 g (0.20 mol) of 3-(4-cyano-2,5-difluoro-phenyl)-2-dimethyl-amino-6-trifluoromethyl-pyrimidin-4-one and 300 ml of N,N-dimethyl-formamide is admixed dropwise with stirring with 9 ml of conc. hydrochloric acid, stirred in the temperature range stated for about another three hours and then stirred into 1800 ml of ice-water. The resulting crystalline product is isolated by filtration with suction.

This gives 71.1 g (84.5% pure, i.e. 83% of theory) of N-(4-cyano-2,5-difluoro-phenyl)-3-(dimethylaminocarbonylamino)-4,4,4-trifluoro-2-butenamide of melting point 138° C.

Example (IIb-1)

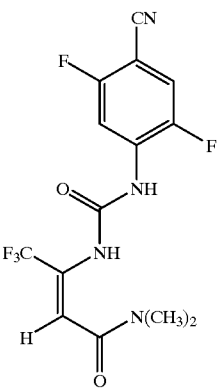

(Process (d))

A solution of 4.2 g (20 mMol) of 2-dimethylamino-4-trifluoromethyl-1,3-oxazin-6-one and 3.1 g (20 mMol) of 4-cyano-2,5-difluoro-aniline in 40 ml of 1,2-dimethoxy-ethane is heated to the boil with stirring, for 24 hours. After cooling, the resulting crystalline product is isolated by filtration with suction.

This gives 3 g (52.5% of theory) of N,N,-dimethyl-3-(4cyano-2,5difluoro-phenyl-amino-carbonylamino)-4,4,4-trifluoro-2-butenamide of melting point 198° C.

Example (IIb-2)

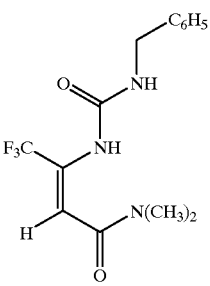

(Process (d))

A solution of 1.0 g (5 mMol) of 2-dimethylamino-4-trifluoromethyl-1,3-oxazin-6-one and 0.54 g (5 mMol) of benzylamine in 10 ml of 1,2-dimethoxy-ethane is stirred at 25° C. for 2 hours. The mixture is subsequently concentrated under water pump vacuum and the residue is taken up in methylene chloride and filtered through silica gel. The solvent is carefully distilled off from the filtrate under water pump vacuum.

This gives 1.0 g (95.8% pure, i.e. 67% of theory) of N,N-dimethyl -3-(benzylaminocarbonylamino)-4,4,4-trifluoro-2-butenamide as an oily residue.

Example (III-1)

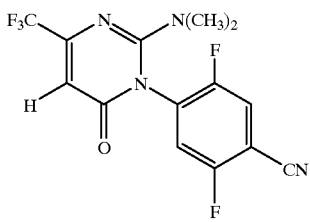

156 g (0.96 mol) of dichloromethylene-dimethylimmonium chloride (phosgeneimmonium chloride) are initially charged in 1200 ml of chloroform and, at room temperature (about 20° C. to 30° C.) admixed a little at a time with stirring with 203 g (0.60 mol) of N-(4-cyano-2, 5-difluoro-phenyl)-3-amino-4,4,4-trifluoro-2-butenamide. The reaction mixture is then stirred at 40° C. (evolution of gas) for 90 minutes and under reflux for two hours. At room temperature, the mixture is then stirred with 170 ml of saturated aqueous sodium bicarbonate solution and the organic phase is separated off washed with saturated aqueous sodium bicarbonate solution and then with water and concentrated under water pump vacuum. The residue is stirred with 300 ml of diisopropyl ether and the crystalline product is isolated by filtration with suction.

This gives 189 g (93.9% pure, i.e. 86% of theory) of 3-(4-cyano-2,5-difluoro-phenyl)-2-dimethylamino-6-trifluoromethyl-pyrimidin-4-one of melting point 147° C.

Starting materials of the formula (IV):

Example (IV-1)

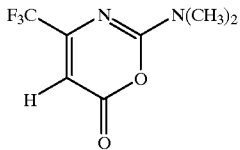

24.4 g (150 mMol) of dichloromethylene-dimethylimmonium chloride are suspended in 130 ml of 1,2-dimethoxy-ethane and, at 25° C., admixed dropwise with stirring over a period of about 40 minutes with a solution of 25 g (136 mMol) of ethyl 4,4,4-trifluoro-2-butenoic acid in 130 ml of 1,2-dimethoxy-ethane. With stirring, the reaction mixture is heated to the boil for 12 hours. After cooling, the solvent is carefully distilled off under water pump vacuum, the crystalline residue (27 g) is digested with hexane and the product is isolated by filtration with suction.

This gives 22.6 g (80% of theory) of 2-dimethylamino-4-trifluoromethyl-1,3-oxazin-6-one of melting point 79° C.

Starting materials of the formula (VI):

Example (VI-1)

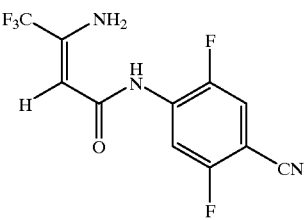

Step 1

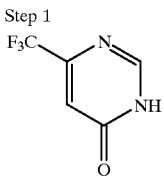

At room temperature (about 20° C.), a mixture of 564 g (3.0 mol) of ethyl 4,4,4-trifluoro-acetoacetate, 472 g (4.5 mol) of formamidine acetate and 3800 ml of methanol is, with stirring, mixed a little at a time with 382 g (3.81 mol) of sodium carbonate, and the reaction mixture is stirred at 60° C. for 15 hours. At from 5° C. to 10° C., the mixture is then acidified with 780 ml of conc. hydrochloric acid and then concentrated under water pump vacuum. The residue is stirred with 2700 ml of ethyl acetate and 1200 ml of water, the organic phase is separated off and the solvent is carefully distilled off from the organic phase under water pump vacuum.

This gives 473 g (100% pure, i.e. 96% of theory) of 6-trifluoromethyl-pyrimidin-4-one as a solid residue of melting point 169° C.

Step 2

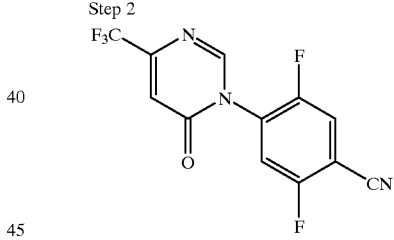

Variant (a)

At room temperature (about 20° C. to 30° C.), a solution of 472 g (2.88 mol) of 6-trifluoromethyl-pyrimidin-4-one in 2300 ml of dimethyl sulphoxide is, with stirring, admixed a little at a time with 398 g (2.88 mol) of potassium carbonate, and the mixture is stirred at room temperature for 20 minutes. 466 g (2.88 mol) of 2,4,5-trifluoro-benzonitrile are then added thereto a little at a time, and the reaction mixture is stirred at 60° C. for 18 hours and subsequently added to 9 liters of ice-water. The resulting crystalline (crude) product is, after about one hour, isolated by filtration with suction and dried under water pump vacuum. For purification, the product is stirred with 3 liters of isopropanol/water (1:1) for 5 hours, again filtered off with suction and dried at 40° C. under water pump vacuum.

This gives 655 g (80.2% pure, i.e. 63% of theory) of 3-(4-cyano-2,5-difluoro-phenyl)-6-trifluoromethyl-pyrimidin-4-one of melting point 144° C.

Variant (b)

At room temperature (about 20° C. to 30° C.), a solution of 32.8 g (0.20 mol) of 6-trifluoromethiyl-pyrimidin-4-one in 160 ml of dimethyl sulphoxide is, with stirring, admixed a little at a time with 22.4 g (0.20 mol) of potassium t-butoxide, and the mixture is stirred at room temperature for 20 minutes. 35.5 g (0.25 mol) of 2,4,5-trifluoro-benzonitrile are then added thereto a little at a time, and the reaction mixture is stirred at from 60° C. to 70° C. for 10 hours and subsequently added to 650 ml of ice-water. The resulting crystalline (crude) product is, after about one hour, isolated by filtration with suction and dried under water pump vacuum. For purification, the product is stirred with 600 ml of isopropanol and 300 ml of water for 10 minutes, once more filtered off with suction and dried at 40° C. under water pump vacuum.

This gives 42.9 g (89.9% pure, i.e. 64% of theory) of 3-(4-cyano-2,5-difluoro-phenyl)-6-trifluoromethyl-pyrimidin-4-one of melting point 144° C.

Step 3

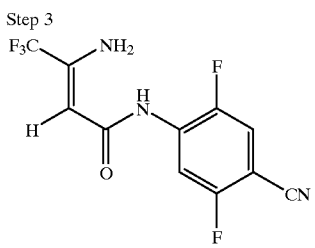

652 g (1.75 mol) of 3-(4cyano-2,5-difluoro-phenyl)-6-trifluoromethyl-pyrimidin-4-one are suspended in 9 liters of water and, at room temperature (about 20° C. to 30° C.), admixed dropwise with 201 ml of conc. aqueous sodium hydroxide solution (3.33 mol of NaOH). The reaction mixture is stirred at room temperature for 15 hours and subsequently filtered off with suction. The filter cake is taken up in 2300 ml of toluene, and the solution is dried using a water separator. The product, which is obtained in crystalline form on cooling (finally to about 5° C.), is isolated by filtration with suction.

This gives 530 g (86.1% pure i.e. 89.5% of theory) of N-(4-cyano-2,5-difluoro-phenyl)-3-amino-4,4,4-trifluoro-2-butenamide of melting point 170° C.

What is claimed is:

1. A process for preparing a substituted aminoalkenamide of the formula (IIa)

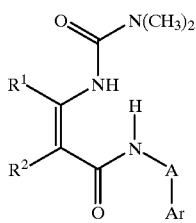

(IIa)

comprising reacting a substituted pyrimidone of the formula (III)

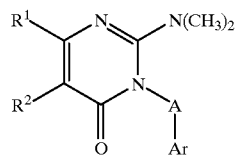

(III)

wherein

A represents a single bond or represents alkanediyl,

Ar represents optionally substituted aryl, $R^1$ represents optionally substituted alkyl and $R^2$ represents hydrogen, halogen or alkyl, at temperatures between 0° C. and 100° C. with an acid, if appropriate in the presence of a diluent.

2. A process for preparing a substituted aminoalkenamide of the formula (IIb)

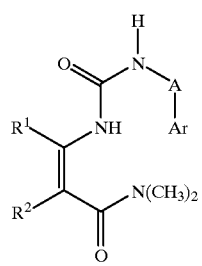

(IIb)

comprising reacting a substituted oxazinone of the formula (IV)

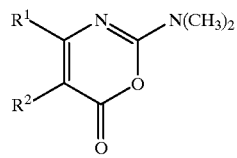

(IV)

wherein $R^1$ represents optionally substituted alkyl and $R^2$ represents hydrogen, halogen or alkyl, with an ar(alk)ylamines of the formula (V)

$H_2N-A-Ar$ (V)

wherein

A represents a single bond or represents alkanediyl, and

Ar represents optionally substituted aryl, at temperatures between 0° C. and 150° C., if appropriate in the presence of a diluent.

3. A substituted pyrimidone of the (III)

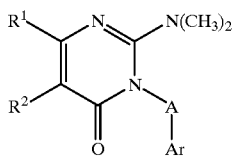

(III)

wherein

A represents a single bond or represents alkanediyl,
Ar represents optionally substituted aryl,
$R^1$ represents optionally substituted alkyl and
$R^2$ represents hydrogen, halogen or alkyl.

4. A process for preparing a substituted pyrimidone of the formula (III)

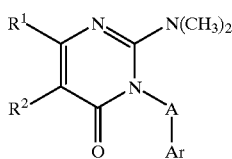

(III)

comprising reacting a substituted aminoalkenamide of the formula (VI)

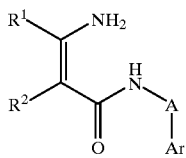

(VI)

wherein

A represents a single bond or represents alkanediyl,
Ar represents optionally substituted aryl,
$R^1$ represents optionally substituted alkyl and
$R^2$ represents hydrogen, halogen or alkyl with dichloromethylene-dimethylimmonium chloride of the formula (VII)

(VII)

at temperatures between 0° C. and 100° C. in the presence diluent.

5. A process for preparing a ar(alk)yluracil of the formula (I)

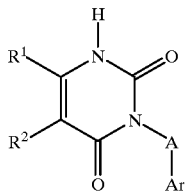

(I)

wherein

A represents a single bond or represents alkanediyl,
Ar represents optionally substituted aryl,
$R^1$ represents optionally substituted alkyl and
$R^2$ represents hydrogen, halogen or alkyl, comprising the steps of:

a) reacting a substituted aminoalkenamide of the general formula (VI)

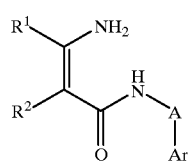

(VI)

wherein A, Ar, $R^1$ and $R^2$ are as defined above with dichloromethylene-dimethylimmonium chloride of the formula (VII)

at temperatures between 0° C. and 100 °C. in the presence of a diluent;

b) reacting the substituted pyrimidone of the formula (III) prepared in step a)

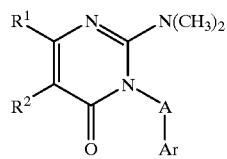

(III)

wherein A, Ar, $R^1$ and $R^2$ are as defined above at temperatures between 0° C. and 100° C. with an acid, if appropriate in the presence of a diluent, and c) heating of the substituted aminoalkenamide of the general formula (IIa) prepared in step b)

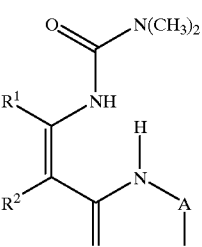

(IIa)

wherein A, Ar, $R^1$ and $R^2$ are as defined above at temperatures between 40° C. and 120° C., if appropriate in the presence of a diluent.

* * * * *